US012414928B2

(12) United States Patent
Javier

(10) Patent No.: US 12,414,928 B2
(45) Date of Patent: Sep. 16, 2025

(54) VIRAL INACTIVATION SPRAY AND GARGLING FORMULATION

(71) Applicant: Rene Dumalaog Javier, Parkville, MD (US)

(72) Inventor: Rene Dumalaog Javier, Parkville, MD (US)

( * ) Notice: Subject to any disclaimer, the term of this patent is extended or adjusted under 35 U.S.C. 154(b) by 0 days.

(21) Appl. No.: 17/663,565

(22) Filed: May 16, 2022

(65) Prior Publication Data

US 2022/0362190 A1   Nov. 17, 2022

Related U.S. Application Data

(60) Provisional application No. 63/201,833, filed on May 14, 2021.

(51) Int. Cl.
| | |
|---|---|
| *A61K 31/198* | (2006.01) |
| *A61K 9/00* | (2006.01) |
| *A61K 9/08* | (2006.01) |
| *A61K 31/194* | (2006.01) |
| *A61P 31/14* | (2006.01) |

(52) U.S. Cl.
CPC .......... *A61K 31/198* (2013.01); *A61K 9/0043* (2013.01); *A61K 9/08* (2013.01); *A61K 31/194* (2013.01); *A61P 31/14* (2018.01)

(58) Field of Classification Search
CPC ...... A61K 31/198; A61K 9/0043; A61K 9/08; A61K 31/194; A61K 9/0053; A61P 31/14
See application file for complete search history.

(56) References Cited

U.S. PATENT DOCUMENTS

| | | | |
|---|---|---|---|
| 8,669,045 | B2 | 3/2014 | Koyama et al. |
| 9,462,810 | B2 * | 10/2016 | Koyama ............... C12N 7/04 |
| 9,872,499 | B2 | 1/2018 | Ejima et al. |
| 2005/0232868 | A1 | 10/2005 | Rennie et al. |
| 2007/0274926 | A1 | 11/2007 | Fuls et al. |
| 2009/0226538 | A1 | 9/2009 | Park |
| 2009/0232748 | A1 | 9/2009 | Capps |
| 2010/0204323 | A1 | 8/2010 | Theiler et al. |
| 2016/0010063 | A1 | 1/2016 | Selvitelli et al. |
| 2016/0166624 | A1 | 6/2016 | Schwartz |
| 2020/0000751 | A1 | 1/2020 | Ernst |
| 2021/0299156 | A1 | 9/2021 | Bates et al. |
| 2021/0347858 | A1 | 11/2021 | Starzl |
| 2021/0386667 | A1 | 12/2021 | Vega |
| 2022/0000827 | A1 | 1/2022 | Strobel et al. |
| 2022/0040065 | A1 | 2/2022 | Shewale et al. |
| 2022/0040135 | A1 | 2/2022 | Rau et al. |

FOREIGN PATENT DOCUMENTS

JP   2009263231 A   11/2009

OTHER PUBLICATIONS

Eaton et al (Eaton, M.D., Scala, A.R. & Low, I.E. Archiv f Virusforschung 14, 583-598 (1964)) (Year: 1964).*
Melano (Viruses, 2021, 13, 1301), (Year: 2021).*
Roda. Phys. Chem. Phys., Jan. 2021, 23, 1706). (Year: 2021).*
John Hopkins Medicine (Coronavirus Diagnosis: What Should I Expect, Updated Jan. 24, 2022, John Hopkins Medicine, url=https://www.hopkinsmedicine.org/health/conditions-and-diseases/coronavirus/diagnosed-with-covid-19-what-to-expect, accessed Nov. 29, 2024 (Year: 2022).*
Miriam E.R. Darnell et al, "Inactivation of the coronavirus that induces severe acute respiratory syndrome, SARS-COV", Journal of Virological Methods, vol. 121, Issue 1, 2004, pp. 85-91.
Rennie, P., et al. "Low pH gel intranasal sprays inactivate influenza viruses in vitro and protect ferrets against influenza infection." Respir Res 8, 38 (2007).
Stegmann, T.et. al. "Effects of Low pH on Influenza Virus—Activation and Inactivation of the Membrane Fusion-Capacity of the Hemagglutinin" Dec. 25, 1987, The Journal of Biological Chemistry. 262, 36, p. 17744-17749.
James E. Gern, et al., "Inhibition of Rhinovirus Replication In Vitro and In Vivo by Acid-Buffered Saline", The Journal of Infectious Diseases, vol. 195, Issue 8, Apr. 15, 2007, pp. 1137-1143.
Satoshi Ohtake et al., "Arginine as a Synergistic Virucidal Agent", Mar. 2010, Molecules 15(3):1408-24.
Shao A, Hathcock JN (Apr. 2008). "Risk assessment for the amino acids taurine, L-glutamine and L-arginine". Regulatory Toxicology and Pharmacology. 50 (3): 376-99.
Guoyao Wu et al., "Arginine deficiency in preterm infants: biochemical mechanisms and nutritional implications" J Nutr Biochem. Aug. 2004; 15(8):442-51.
Anneke J A H van Vught et al., "Dietary arginine and linear growth: the Copenhagen School Child Intervention Study", Br J Nutr. Mar. 28, 2013; 109(6):1031-9.
Yamasaki, H., Tsujimoto, K., Koyama, A. H., Ejima, D., & Arakawa, T. (2008). Arginine facilitates inactivation of enveloped viruses. Journal of Pharmaceutical Sciences, 97(8), 3067-3073. https://doi.org/10.1002/jps.21224.

* cited by examiner

*Primary Examiner* — Jeffrey H Murray
*Assistant Examiner* — Luisalberto Gonzalez
(74) *Attorney, Agent, or Firm* — Dunlap Bennett & Ludwig, PLLC; Anna L. Kinney

(57) ABSTRACT

A viral inactivation composition includes an aqueous solution of citric acid and L-arginine hydrochloride with a pH below 3.5. The citric acid and L-arginine hydrochloride are present in amounts that directly inactivate COVID-19, influenza, and common cold virus in a human upper respiratory system. A method of directly inactivating COVID-19, influenza, and common cold virus in the human upper respiratory system includes administering the viral inactivation composition to a subject. These ingredients are safe, non-toxic, and very effective.

5 Claims, 2 Drawing Sheets

VIRAL INACTIVATION SPRAY AND GARGLING FORMULATION

CROSS-REFERENCE TO RELATED APPLICATION

This application claims the benefit of priority of U.S. provisional application No. 63/201,833, filed May 14, 2021, the contents of which are herein incorporated by reference.

BACKGROUND OF THE INVENTION

The present invention relates to a virus inactivation formulation and, more particularly, to a viral inactivation spray and gargling formulation.

Viruses that have made their way into the nose and mouth adhere to the epithelial cells of the nasal cavities and the pharynx. Depending upon the kind of virus, degree of exposure and the duration, the virus eventually delivers its genetic materials into the host's epithelial cells for replication. Inactivating the virus at the nasal cavities and the pharynx where they start is the most effective way of preventing and stopping an infection.

Many nasal sprays only try to alleviate the symptoms but do not stop the main underlying cause of a viral infection.

Recent research by the United States Food and Drug Administration (FDA) and National Institutes of Health (NIH) with coronavirus disease 2019 (COVID-19) reported 100% virus inactivation in vitro at pH<3.0 with the use of Hydrochloric Acid. (See Miriam E. R. Darnell et al, "Inactivation of the coronavirus that induces severe acute respiratory syndrome, SARS-CoV", Journal of Virological Methods, Volume 121, Issue 1, 2004, Pages 85-91.) Although Hydrochloric Acid is a highly effective virus inactivator in vitro, it is a strong acid that is very damaging to the human tissues. Strong acids are identified by their negative pKa values. Hydrochloric Acid, Nitric Acid, and Perchloric Acid have pKa values of −5.9; −1.4; and −15 respectively.

As pH<3.0 is a very significant factor in the enveloped virus inactivation, using components that are safe, non-toxic, and do not harm the human tissues are of utmost importance.

A study showed that the Human Influenza A Virus was inactivated up to 5-log reduction with phosphate buffered solutions at pH 3.5 that were administered intranasally to ferrets. (See Rennie, P., et al. "Low pH gel intranasal sprays inactivate influenza viruses in vitro and protect ferrets against influenza infection." Respir Res 8, 38 (2007).) Acid formulations based on L-pyroglutamic acid with ascorbic acid, phytic acid, citric acid, and succinic acid were used, as well as other formulations containing gelling agents and additives. It was found that viral inactivation at pH 3.5 induced conformational change to the viral Hemagglutinin that inhibits binding to the host cell surface. Electron microscopic examination of virus at low pH and 98 degrees Fahrenheit showed fusion activity of Hemagglutinin to be irreversibly lost. (Stegmann, T. et. al. "Effects of Low pH On Influenza Virus—Activation and Inactivation of the Membrane Fusion—Capacity of the Hemagglutinin" 25 Dec. 1987, The Journal of Biological Chemistry. 262, 36, p. 17744-17749.)

Clinical studies with men and women volunteers, from 18 to 60 years of age, were conducted to determine tolerability of low-pH nasal sprays with citric acid/L-pyroglutamic acid/phytic acid solutions at pH of 3.5. (See James E. Gern, et al., "Inhibition of Rhinovirus Replication In Vitro and In Vivo by Acid-Buffered Saline", The Journal of Infectious Diseases, Volume 195, Issue 8, 15 Apr. 2007, Pages 1137-1143.) According to this study, "the sprays were generally well tolerated, and all subjects completed all phases of the study".

In the search for other non-toxic and effective virus inactivators, L-Arginine, a natural amino acid, has been found to inactivate virus and is safe for human use. It has unique properties that enhance virus inactivation at low pH and at normal human body temperature (i.e., about 98.6° F.). An in vitro study showed enveloped virus inactivation of 5 logs reduction at a pH of 3.8 can also be achieved with L-Arginine at pH 4.0. (Satoshi Ohtake et al., "Arginine as a Synergistic Virucidal Agent", March 2010, Molecules 15(3): 1408-24.)

United States Publication No. 20220040135 is directed to a skin and wound healing composition comprising decanoic acid and arginine with a pH of from 6 to 10.

United States Publication No. 20160010063 is drawn to a composition in which the main ingredient is a recombinant blood coagulation factor antibody with detergents and pH buffers. Arginine with 50% weight by volume of glycol is used in producing the antibody with respect to purifying or inactivating virus therein. The composition further comprises detergents and other additives.

U.S. Pat. No. 9,872,499 teaches a virus-inactivating composition with pH of 3.8 to 5.5, containing arginine, flavonoid, polyphenol, or ascorbic acid derivative, 0.005 to 5 mass % of acyl arginine, and 0.1 to 2.5 mass % of an extract solution of natural product such as tea and essential oils. As discussed in Japanese Patent Unexamined Publication ("JP Kokai") No. 2009-263231 and Journal of Pharmaceutical Sciences, 97, 3067-3073 (2008) mentioned in this patent, Arginine or Arginine derivatives are used for a key step in the purification of pharmaceutical proteins. Acylated arginine, such as the acyl arginine of U.S. Pat. No. 9,872,499, is also referred to herein as R—C=O-Arginine.

U.S. Pat. No. 8,669,045 discloses preparation of immunoglobulin formulations. During the manufacture of protein formulations, an Acylated Arginine from the group consisting of N.alpha.-acetyl-L-arginine, N.alpha.-butyroyl-L-arginine, N.alpha.-pivaloyl-L-arginine, N.alpha.-valeroyl-L-arginine, and N.alpha.-caproyl-L-arginine is adjusted for pH within 3.5 to 5 and used for virus inactivation.

There is no commercially available formulation that is safe and non-toxic that can directly inactivate the virus where potential infection occurs: the nasal cavities and the pharynx.

As can be seen, there is a need for a safe, non-toxic formulation that can directly inactivate a virus in the nasal cavities and the pharynx.

SUMMARY OF THE INVENTION

In one aspect of the present invention, a viral inactivation composition comprises an aqueous solution of citric acid and L-arginine hydrochloride with a pH below 3.5. The citric acid and L-arginine hydrochloride are present in amounts effective to directly inactivate COVID-19, influenza, and common cold virus in a human upper respiratory system.

In another aspect of the present invention, a method of directly inactivating COVID-19, influenza, and common cold virus in the human upper respiratory system comprises administering the viral inactivation composition to a subject.

The inventive composition may also be applied to animals that are infected with the virus, which may provide a way to eradicate the virus as it is known to mutate and transfer across different species.

These and other features, aspects and advantages of the present invention will become better understood with reference to the following drawings, description, and claims.

DETAILED DESCRIPTION OF THE INVENTION

Figure 1:
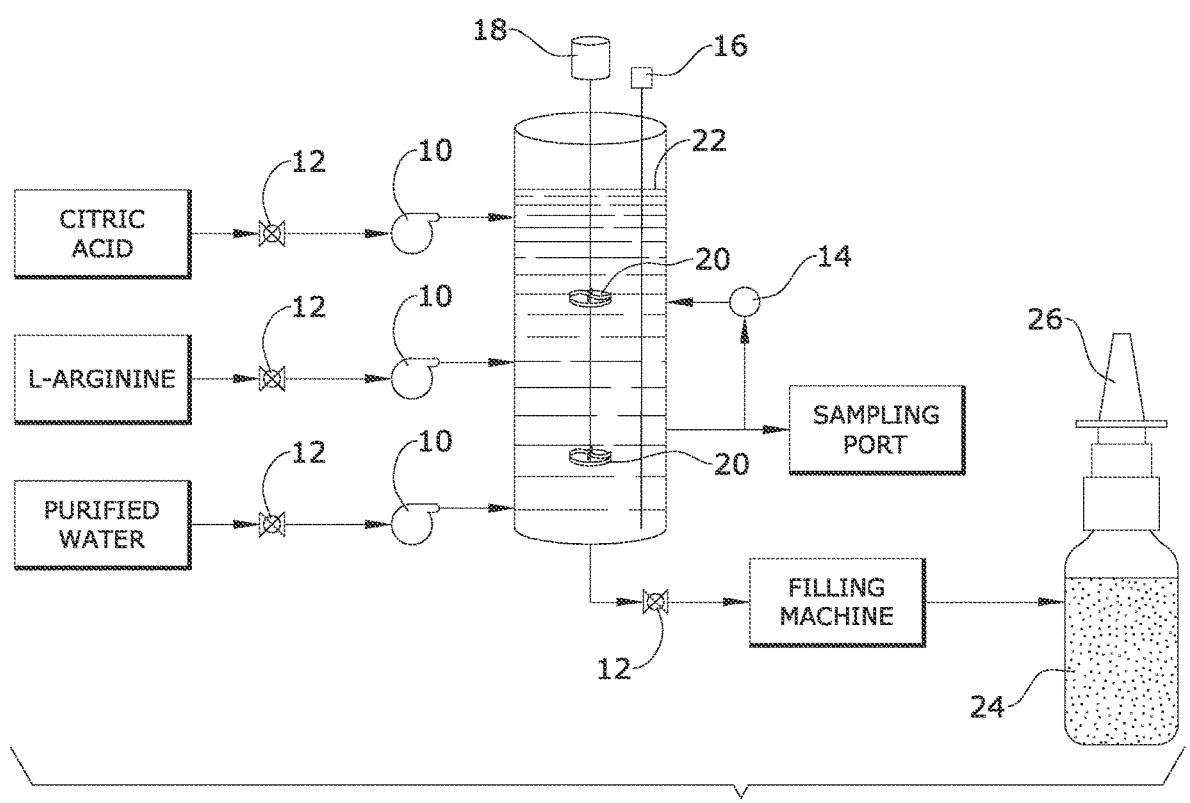
FIG. 1 is a schematic illustration of a process of manufacturing a nasal spray according to the present invention.

The following detailed description is of the best currently contemplated modes of carrying out exemplary embodiments of the invention. The description is not to be taken in a limiting sense but is made merely for the purpose of illustrating the general principles of the invention, since the scope of the invention is best defined by the appended claims.

Broadly, one embodiment of the present invention is a viral inactivation composition administered as a spray and gargling formulation such that it is effective to directly inactivate COVID-19, influenza, and common cold virus in the human upper respiratory system. The inventive formulation comprises Citric Acid and L-Arginine hydrochloride (HCl) which are natural food nutrients combined in an aqueous solution to achieve the high degree of viral inactivation without any harmful effects on the human body, as the ingredients are metabolized by the human tissues as food. These ingredients are safe, non-toxic, and very effective.

The inventive components have very high affinity to the viral membrane lipids and spike proteins. Direct contact application of this novel formulation with the virus is a fast and effective delivery method in preventing or stopping an early infection. The composition has been found to relieve symptoms and inactivate the virus within minutes. Application of this novel formulation on asymptomatic or early infected individuals is effective to significantly reduce the spread of the virus from close human interactions.

The inventive composition is sometimes referred to herein as "PREV-Vi". "(S)" is used to refer to a spray and "(G)" is used to refer to a gargling solution. PREV-Vi is a potent viral inactivator that is safe, non-toxic, and does not harm the human tissues when applied directly on infection sites of the nasal cavities and the pharynx.

The inventive formulation generally has a pH in a range of about 2.8 to about 3.4. As previously noted, the pH range is low, preferably below about 3.5 or about 3, e.g., a pH of 2.92, to provide effective inactivation of the virus. This combination of L-Arginine(HCl) and Citric Acid at a pH of 2.92 induce the virus' fusion activity of its Hemagglutinin to irreversibly be lost, destroy the virus' lipid membrane, and react with the viral proteins, thereby irreversibly inactivating the virus' capability of replication and mutation. Low pH of 2.92 ensures virus inactivation considering that the formulation gets partially diluted by the natural body fluids when applied in the nasal cavities and in the pharynx.

The proportions of Citric Acid, L-Arginine, and purified water may be varied to target other viruses and bacteria or for specific applications. For example, the proportions may be adjusted by adding more purified water to reach a pH of 2.95 for children. Another application may be adding more Citric Acid, e.g., for a specific mutant virus and adjusting the pH down to 2.85. Another application may be having less purified water for dilution to reduce pH for more potency. For example, the ratio of Citric Acid to L-Arginine to purified water may be changed slightly to target a lower pH than 2.92, for example 2.65. This pH of 2.65 may be used if there is a mutant virus that is more resistant to a pH of 2.92. This is still believed to be a safe level since lime and lemon juice pH may be as low as 2.4.

Food Grade Citric Acid serves as a pH buffer and breaks up the viral envelope.

Pharmaceutical Grade L-Arginine(HCl) in the formulation is catalyzed by Citric Acid's low pH to bind into the virus' phosphate components and insert into the lipid membrane. It is then incorporated into the viral proteins during translation. On the other hand, L-Arginine(HCl) passivates and protects the human tissues from the hydrogen ions and neutralizes the harmful protein component of the virus. The inventive composition requires Arginine-HCl which has entirely different physical and chemical properties from other chemical forms of Arginine, such as an Acylated Arginine.

The inventive composition generally excludes other ingredients such as decanoic acid, glycols, detergents, buffers, and flavors.

Depending on duration and degree of exposure, early symptoms of viral infection such as itchy or stuffy nose, congestion, and sore throat may be effectively relieved by this virus inactivator formulation. The best probability of preventing viral infection may be achieved by applying PREV-VI(S) and (G) daily before bed; any time symptoms become apparent; and within 4 to 16 hours upon any suspected exposure in a crowd, with an infected person, or in an unventilated virus contaminated space area. Relief from the symptoms may be felt within minutes from the time of application.

The virus inactivator may be applied in the nasal cavities by nasal spray and in the pharynx by gargling solution upon exposure to the virus.

A subject may use one or two full sprays in each nostril once a day or upon any suspected exposure. One dose spray of PREV-Vi(S) is about 50 mcg. After applying into the nostrils, the subject may use 5 to 10 ml of PREV-Vi (G) to gargle.

When gargling, the subject may hold the solution for about 1 minute. When severe itchy or sore throat is felt, a 5-10 ml amount of PREV-Vi (G) may be gargled for a duration of about 30 to 60 seconds up to three times. The 3rd gargle may be swallowed, flushing any virus in the throat. One dispensing cup of PREV-Vi(G) may be about 5 to 10 ml.

If symptoms persist, the subject may repeat every half hour. After a third or fourth application has been made, the subject may apply the formulation in about 4-hour intervals until symptoms have been relieved.

PREV-Vi(S) and (G) may be stored at normal room temperatures (i.e., about 70° F.) and are best applied at 80 to 95 degrees Fahrenheit.

Example 1: Preparation of Virus Inactivator Composition for Covid-19 and Influenza Viruses PREV-Vi Formulation 1 may be composed of 10.00 units by weight Citric Acid to 51.4 units by weight L-Arginine (HCl). This combined weight of Citric Acid plus L-Arginine (HCl) of 61.4 units is dissolved in an initial volume of 614 units by weight of purified water in a closed container such as a mixing tank. The pH of this solution may be determined using a pH meter and a pH controller. For example, after 15 minutes of stirring, pH is read and adjusted. While stirring, the pH meter and controller determine whether to slowly add either more purified water or Citric-Arginine mix until a pH of 2.92±0.01 is reached.

TABLE 1

| Material | Quantity |
| --- | --- |
| Citric Acid | 1.00 lb. |
| L-Arginine | 5.14 lb. |
| Purified water* | 61.4 lb. |

*Calculated as 10 × subtotal of citric acid + L-Arginine quantities (e.g., to 6.14 pounds Citric-Arginine mixture, add 61.4 pounds water.)

Improvement may be determined in clinical trials by applying PREV-Vi formulation with a nebulizer.

Example 2: Application

A couple attended a crowded event inside a building. They stayed for about 6 hours. When the couple left, one person felt soreness and itch in his throat. He administered three spray doses of PREV-Vi, one to each nostril at a time, breathing air after spraying with the chin up, holding one nostril at a time. He blew his nose a minute after the first spray.

Example 3: Safety and Efficacy

Six volunteers already experiencing symptoms for more than 7 days tested positive on a COVID-19 antigen test. The volunteers, 3 men and 3 women, ranged in age from 23 thru 49 years old. Vaccination status varied: 2 volunteers were not vaccinated, the other 4 volunteers had vaccines. Of the 4 vaccinated volunteers, 3 had their booster shots.

All 6 volunteers started using Prev-Vi about 3 days after confirmation of a positive antigen test. All 6 felt better after 24 hours of use as they experienced significant decrease in coughing and sore throat and were able to breath better. All 6 said that all symptoms were gone after 3-5 days of use and that they believe that they have recovered 100% of their normal health. All 6 tested negative with the same COVID-19 antigen test after 7 to 10 days of use. None of the volunteers complained of any adverse side effect and none experienced long COVID-19 a month after testing negative from COVID-19.

Example 4: Prophylactic Use

Twenty-nine volunteers, 14 men and 15 women, used Prev-Vi to prevent infections. Volunteers within the age range of 6 to 11 years included two unvaccinated boys and one unvaccinated girl. Nine vaccinated volunteers were 61 years or older. Of 17 volunteers within the age range of 17 to 60 years, 2 were not vaccinated.

All 29 volunteers used Prev-Vi right after attending highly populated gatherings, after getting exposed to an infected person, or before going on interstate travel. Some experienced sneezing and sore throat 1-2 days after an exposure; these symptoms were relieved within 30 minutes after applying Prev-Vi. Those that experienced symptoms for about 3-5 days obtained relief from symptoms within 24 hours of application. Some did not experience any symptoms but used the inventive composition anyway after attending gatherings and during their travels. These volunteers did not get any COVID-19 infection. All volunteers agreed that the inventive composition is safe and very effective in preventing an infection and none reported an adverse side effect.

Figure 2:
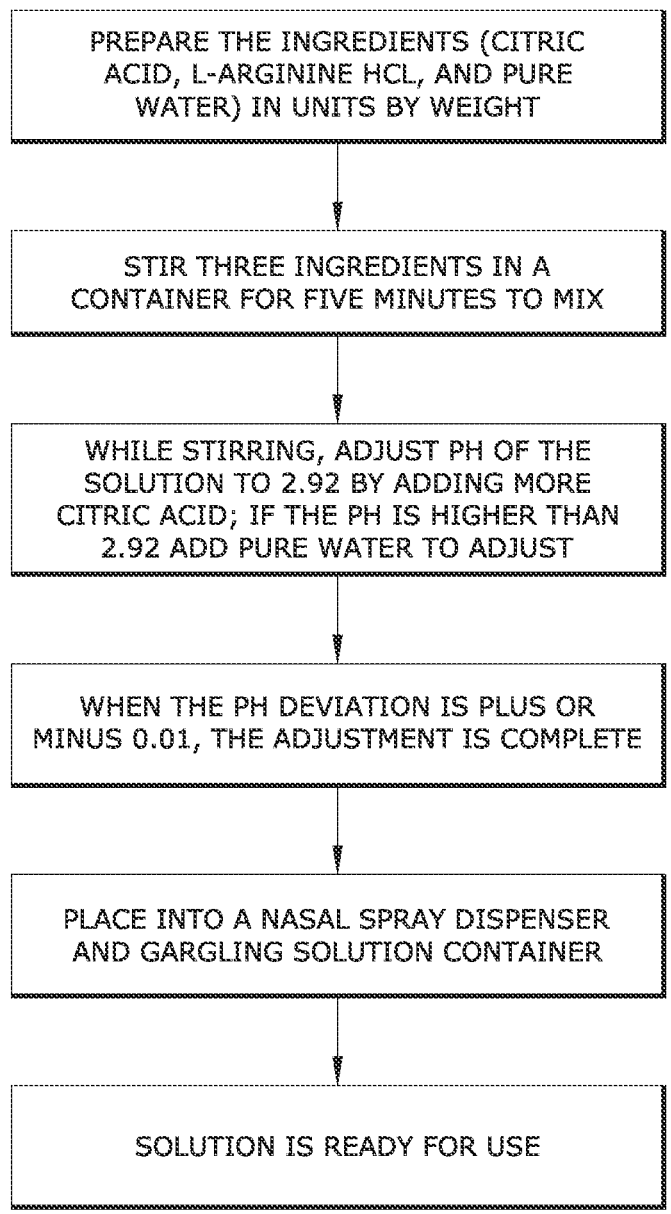
FIG. 2 is a flow chart thereof.

Referring to FIGS. 1 and 2, FIG. 1 is a schematic view illustrating manufacture of a composition according to an embodiment of the present invention. Metering pumps 10 with remote controlled valves 12 deliver flows of citric acid, L-arginine, and purified water to a stainless-steel batch mixing tank having motor 18 driven impellers 20. The flow rates may be based on predetermined ratios and optimized to achieve a predetermined pH. As discussed in FIG. 2, the ingredients may be mixed for about 5 minutes. A timer and pH controller 14 and sampling port ensure that the resulting composition has a predetermined pH value and component ratio. A level indicator 16 ensures that the composition volume is sufficient to be effectively mixed and low enough to avoid spilling over. Mixed liquid 24 may be extracted from the tank to file a nasal spray bottle 26.

It should be understood, of course, that the foregoing relates to exemplary embodiments of the invention and that modifications may be made without departing from the spirit and scope of the invention as set forth in the following claims.

What is claimed is:

1. A viral inactivation composition for administration to a human upper respiratory system, comprising an aqueous solution of citric acid and L-arginine hydrochloride, wherein the L-arginine hydrochloride is present in an amount of 5.14 parts by weight per about 1 part by weight of the citric acid; and wherein water is present in an amount of at least 10 parts by weight per combined part by weight of the L-arginine and the citric acid; and wherein the citric acid and the water amounts are adjusted to obtain a pH between 2.65 and 2.95.

2. The viral inactivation composition of claim 1, wherein the aqueous solution lacks decanoic acid, glycols, detergents, non-citric acid buffers, and flavors.

3. The viral inactivation composition of claim 1, wherein the viral inactivation composition has no buffer other than the citric acid and the L-arginine hydrochloride.

4. The viral inactivation composition of claim 1, wherein the citric acid is present in a concentration of 0.08 M and the L-arginine hydrochloride is present in a concentration of 0.48 M.

5. A viral inactivation composition for administration to a human upper respiratory system, consisting of citric acid at a concentration of 0.08 M, L-arginine hydrochloride at a concentration of 0.48 M, and water; wherein the water is present in an amount of at least 10 parts by weight per combined part by weight of the L-arginine hydrochloride and the citric acid; and wherein the composition is a sprayable liquid at room temperature with a pH between 2.65 and 2.95.

* * * * *